United States Patent
Nurmi et al.

(10) Patent No.: US 6,407,227 B1
(45) Date of Patent: Jun. 18, 2002

(54) PROCESS FOR THE CRYSTALLIZATION OF LACTITOL

(75) Inventors: Juha Nurmi, Pinjainen; Miika Kaira, Espoo, both of (FI)

(73) Assignee: Xyrofin Oy, Kotka (FI)

(*) Notice: Subject to any disclaimer, the term of this patent is extended or adjusted under 35 U.S.C. 154(b) by 0 days.

(21) Appl. No.: 09/380,434

(22) PCT Filed: Mar. 2, 1998

(86) PCT No.: PCT/FI98/00184

§ 371 (c)(1),
(2), (4) Date: Dec. 6, 1999

(87) PCT Pub. No.: WO98/39350

PCT Pub. Date: Sep. 11, 1998

(30) Foreign Application Priority Data

Mar. 3, 1997 (FI) .................................................. 970903

(51) Int. Cl.[7] .............................. C07H 1/08; A23G 3/00
(52) U.S. Cl. ........................ 536/127; 426/658; 514/25; 514/53
(58) Field of Search ............................ 426/658; 514/25, 514/53; 536/127

(56) References Cited

U.S. PATENT DOCUMENTS

| | | | |
|---|---|---|---|
| 5,160,546 A | * 11/1992 | Kawashima et al. | 127/60 |
| 5,494,525 A | * 2/1996 | Heikkila et al. | 127/61 |
| 5,672,589 A | * 9/1997 | Heikkila et al. | 514/53 |
| 5,779,806 A | * 7/1998 | Heikkila et al. | 127/61 |

FOREIGN PATENT DOCUMENTS

| | | |
|---|---|---|
| EP | 0 039 981 | 5/1981 |
| EP | 0 231 643 | 12/1986 |
| EP | 0 456 636 | 8/1989 |
| EP | 0 381 483 | 1/1990 |
| EP | 0 576 473 | 3/1992 |
| JP | 13220/89 | 1/1989 |

OTHER PUBLICATIONS

Kivikoski et al. Crystal structure of lactitol (4–O–beta–D––galactopyranosyl–D–glucitol), Carb. Res., vol. 223: 45–51, 1992.*
Product literature ("Reduced calorie sweetener—Lactitol"), Xyrofin (A division of Cultor Food Science), 1995.*
Ed. Grenby, T.H., "Developments in Sweeteners", 1987, vol. 3, pp. 65–81.
Wolfrom, M.L., et al., *J. Am. Chem. Soc. 60,* 1987, pp. 571–573.
Senderens, J.B., *Compt. Rend 170,* 1920, pp. 47–50.
Wolfrom, M.L. et al., *J. Am. Chem. Soc. 74,* 1952, p. 1105.
Van Velthujisen, J.A., *J. Agric Food Chem. 27,* 1979, p. 680.
Kivikoski, et al., 1992 *Carbohydrate Research 233,* pp. 53–59 and 189–195 (Abstr.).

* cited by examiner

Primary Examiner—Ralph Gitomer
Assistant Examiner—Devesh Khare
(74) Attorney, Agent, or Firm—Scully, Scott, Murphy & Presser

(57) ABSTRACT

The present invention relates to a process for the production of structurally pure lactitol crystal forms selected from the group consisting of anhydrous lactitol, lactitol monohydrate, lactitol dihydrate and lactitol trihydrate. The crystallization is performed by cooling a lactitol solution from a temperature at or slightly below the highest temperature of the stability area of the respective crystalline lactitol form to a temperature at or slightly above the lowest temperature of the stability area of said crystalline lactitol form, said stability areas being defined, respectively, within the temperature limits of 100° C. and 0° C. by the intersections of the solubility lines shown in FIG. 1, and by maintaining the supersaturation of said lactitol solution at a level of 1 to 8% (w/w) above the solubility line of the respective lactitol form crystallizing in said area.

15 Claims, 1 Drawing Sheet

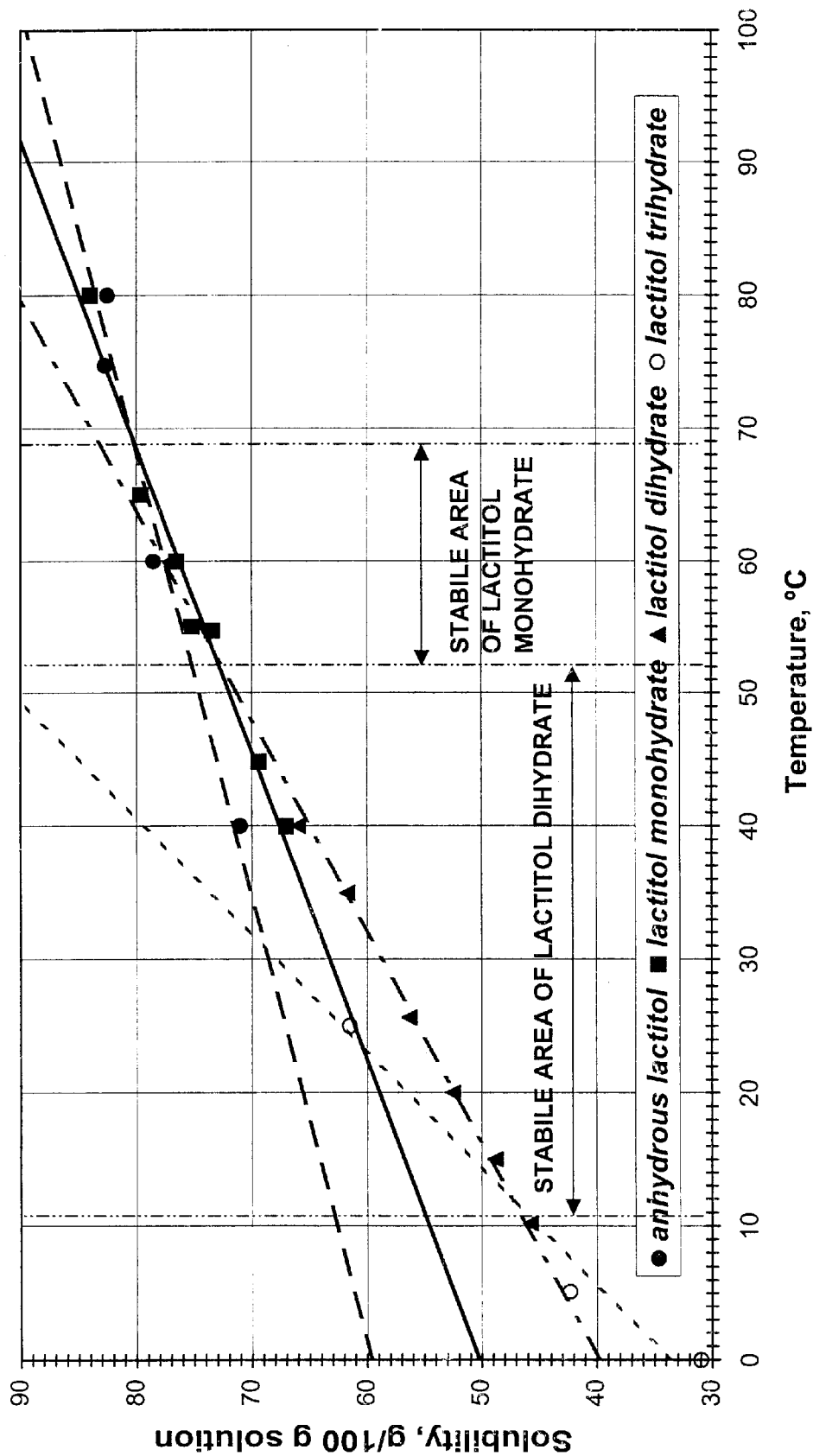

PROCESS FOR THE CRYSTALLIZATION OF LACTITOL

The present invention relates to a process for the production of structurally pure lactitol crystal forms. Especially, the invention comprises a process for the crystallization of lactitol from an aqueous lactitol solution as any one of the crystalline lactitol forms selected from the group consisting of anhydrous lactitol, lactitol monohydrate, lactitol dihydrate and lactitol trihydrate.

Lactitol is a bulk sweetener which can be used as a total or partial replacement for sucrose, however, its energy content is only about half of that of sucrose, and it does not cause increased blood glucose content; furthermore, it is tooth-friendly (see Developments in Sweeteners, Ed. Grenby, T. H., Vol. 3, 1987, p. 65–81).

The preparation of lactitol from lactose has been known for a long time. Industrially, lactitol is prepared analogously with the preparation of sorbitol from glucose by hydrogenation in the presence of a Raney nickel catalyst. The preparation is described e.g. in Wolfrom, M. L., et al., J. Am. Chem. Soc. 60, (1938) p. 571–573.

Crystalline lactitol is reported to occur in the anhydrous form as well as in the form of a monohydrate and dihydrate. Lactitol also crystallizes as a trihydrate. There seem to exist more then one distinct crystalline form at least of the anhydrous form and the monohydrate. In the crystallization, however, the more stable form generally crystallizes predominantly.

Crystalline lactitol monohydrate as well as the di- and trihydrate and the anhydrous form may be used as sweetening agents resembling sugar. For instance, crystalline lactitol monohydrate may be used in dietetic products, confectionery, bakery products, cereals, desserts, jams, beverages, chocolate, chewing gum and ice-cream. The lactitol crystals may also be used in the production of cosmetic products and in the manufacture of pharmaceuticals, such as tooth paste.

According to the above mentioned Wolfrom et al. article anhydrous lactitol can be crystallized by adding ethanol to a lactitol solution evaporated to a high concentration. After a long crystallization time anhydrous lactitol crystals melting between 144 and 146° C. were obtained.

Anhydrous lactitol may also be crystallized from an aqueous solution as described in WO 92/16542, incorporated herein by reference. The process comprises cooling or evaporating a supersaturated lactitol solution at a temperature above 70° C. to provide anhydrous lactitol having a melting range of 149–152° C.

Lactitol hydrate powders anhydrated to a moisture content of less than 3% have been prepared by drying both lactitol solution and crystalline hydrate. The hygroscopicity of these powders is utilized in drying moist mixtures (European Patent Application 0231643).

The crystallization of lactitol dihydrate was presumably mentioned for the first time by Senderens, J. B., Compt. Rend 170, (1920) p. 47–50. Lactitol solution obtained by hydrogenation was evaporated slowly at room temperature so that crystallization was initiated. The melting point of the resulting product was 78° C., and Senderens mistakenly regarded it as a monohydrate. However, it appears obvious from Wolfrom, M. L , et al., J. Am. Chem. Soc. 74 (1952) p. 1105 that the product obtained by Senderers was a dihydrate having a moisture content of 9.5%, determined by a Karl Fischer method, and a melting point between 76 and 78° C.

An attempt to prepare lactitol monohydrate by crystallization was made in 1979, see van Velthuijsen, J. A., J. Agric. Food Chem. 27, (1979) p. 680. The product, however, was an impure hydrate structure containing 4.5% of other sugars.

Another attempt to crystallize lactitol monohydrate was made in 1981 as disclosed in European Patent 0 039 981. The inventors believed that they had obtained pule lactitol monohydrate having a melting point of 121–123° C. However, the crystallization was performed at a constant temperature of 45° C. or 20° C. which, in fact, resulted in the precipitation of a mixture of lactitol-water structures. This product was then dried to provide crystals melting between 110° C. and 125° C. The temperature range indicates that the products were partially anhydrated lactitol hydrate forms. The present applicant has found that it is not possible to produce structurally pure lactitol monohydrate by the processes disclosed in said EP Patent.

EP 0 039 981 also discloses a process for the production of lactitol dihydrate by seeding an aqueous lactitol solution with lactitol dihydrate and crystallizing at a constant temperature between 10 and 25° C. The obtained dihydrates had a melting range of 78–83° C. According to said Patent a lactitol solution provides monohydrate at 25° C. if seeded with monohydrate but dihydrate if seeded with dihydrate. This is contrary to the findings of the present inventors. According to J. Kivikoski et al. in Carbohydrate Research, 233 (1992) 53–59, pure crystalline lactitol dihydrate melts at 70–72° C., which indicates that the dihydrate product of the EP Patent was not structurally pure lactitol dihydrate.

The preparation of lactitol trihydrate is described, for instance, in EP Patent Application 0 381 483. The process comprises crystallization of an aqueous or solvent-containing lactitol solution at a temperature of 0–30° C. The processes according to the Examples use a very high lactitol concentration and obviously may have precipitated besides lactitol trihydrate also a mixture of dihydrate and trihydrate. The melting range of the product was 52–56°C. The structure of lactitol trihydrate has been disclosed in Carbohydrate Research, 233 (1992), 189–195.

The preparation of pure lactitol monohydrate having lattice cell constants a=7.815 Å, b=12.682 Å, and c=15.927 Å; and a melting range between 90 and 100° C., preferably between 94 and 98° C., succeeded for the first time according to the process described in EP Patent 0456636, the disclosure of which is incorporated herein by reference. The melting range was determined, as in the present invention, with a Büchi Tottol melting point apparatus. The lactitol content of the structurally pure lactitol monohydrate was more than 99.5% on a dry substance basis, and its moisture content was between 4.85 and 5.15%.

In the crystallization process according to the invention disclosed in EP 0456636, the crystallization temperatures is in the range from 80 to 30° C. and the crystallization is performed as a cooling crystallization or as an evaporative crystallization. In the examples of said EP Patent 0456636 the lactitol monohydrate of the cooling crystallization was recovered at about 40° C. Since the cooling was rapid at the end of the crystallization and since the crystals present in the solution were pure lactitol monohydrate crystals, the product was pure lactitol monohydrate despite the fact that the temperature was lowered to as low as 40° C. or lower.

The crystallization tests of said EP Patent 0456636 showed that if the crystallization of lactitol monohydrate was to occur in a controlled manner for obtaining a desired crystal size without a wide crystal size distribution, the crystallization should be effected in such a manner that the supersaturation of the mother liquor remained below 1.3 (preferably 1.2) with respect to lactitol throughout the crystallization.

According to JP Application 13220/89 lactitol monohydrate may be produced by crystallizing at a temperature of 20–70° C. to obtain a crystalline product melting at 102–105° C.

The above description of the prior art clearly shows that the crystallization of lactitol is a complex matter, wherein a crystalline product obtained may well be a pure crystalline compound in the form of the pure anhydrous, monohydrate, dihydrate or trihydrate but the crystals may also comprise mixtures of various lactitol-water structures.

Since the literature is full of contradictory statements as regards which temperature ranges and crystallization conditions provide which crystal form, it is evident that the person skilled in the art would benefit from having an exact tool for monitoring the conditions in which to crystallize one or the other of the pure crystal forms.

Such a precision tool for monitoring the crystallization of lactitol between 100 and 0° C. is provided by the present invention, as defined in the appended claims.

The present invention provides the person skilled in the art with a means of solving the problem of knowing when any specific crystalline lactitol form may easily and with certainty be crystallized from a lactitol solution. It provides a tool for the expert to monitor the temperature at any given concentration so as to maintain the supersaturation at a suitable level above the solubility graph of the desired lactitol crystal form.

The specific temperature range for any one of the crystal forms is, according to the invention, provided by the intersections between the respective solubility lines of the adjoining crystal forms and the solubility line of the desired crystal form. The process of the invention allows the person skilled in the art to be sure that the product produced will indeed be structurally pure lactitol crystals of any specific form. The solubility graph disclosed for the first time also shows the restricted area, wherein lactitol monohydrate is the stable crystal form.

A specific feature of the present invention is that it provides a method for crystallizing the crystalline lactitol forms in a pure crystalline form separately from the others at a given temperature interval selected between 100° C. and 0° C.

Thus, the present invention provides a process for the crystallization of lactitol from an aqueous lactitol solution having a lactitol purity of no less than 80% (on DS content), preferably 90% or higher. The crystallization provides structurally pure crystalline lactitol forms selected from the group consisting of anhydrous, monohydrate, dihydrate and trihydrate by cooling said lactitol solution from a temperature at or slightly below the highest temperature of the stability area of the respective crystalline lactitol form to a temperature at or slightly above the lowest temperature of the stability area of said crystalline lactitol form, said stability areas being defined, respectively, within the temperature limits of 1 00° C. and 0° C. by the intersections of the solubility lines defined by the following equations (1) to (4):

anhydrous: $s/\% = 59.6 + 0.3003t/°$ C.   Eq.(1)

monohydrate $s/\% = 50.2 + 0.4346t/°$ C.   Eq.(2)

dihydrate: $s/\% = 39.7 + 0.6332t/°$ C.   Eq.(3)

trihydrate: $s/\% = 33.4 + 1.1482t/°$ C.   Eq.(4)

wherein s is the solubility % (w/w) of each respective lactitol form calculated from the mass of lactitol and water as follows: weight of lactitol/(weight of lactitol+weight of water)×100%;

t is the temperature in ° C.;

and by maintaining the supersaturation of said lactitol solution at a level of 1 to 8% (w/w) above the solubility line of the respective lactitol form crystallizing in said area.

The supersaturation is preferably maintained at the desired level of about 1–8% above the solubility equation by monitoring the temperature and the lactitol concentration of the solution. The supersaturation is preferably held at 7% (w/w) or less. A supersaturation of only 1% will provide a very pure crystal, but the crystallization rate is generally too slow for commercial purposes at such a low supersaturation.

According to a preferred embodiment the supersaturation is maintained at the desired level by monitoring the lactitol content of the lactitol solution and adjusting the temperature accordingly. The lactitol content may be monitored by measuring the refractometric index of the lactitol solution.

In order to ascertain that the desired crystal form is produced from the start of the crystallization and in order to increase the crystallization rate, the lactitol solution is preferably seeded at the start of the crystallization with small crystals of the crystalline lactitol form which is to be crystallized in the respective stability area.

If desired, the cooling crystallization may be preceded by an evaporation crystallization in order to increase the yield of the desired crystal form. The temperature of the evaporation crystallization should preferably be kept well within the stability area of the crystallizing lactitol form, most preferably close to the middle of said stability area, while maintaining the supersaturation at 8% (w/w) or less.

The present invention also provides a process for crystallizing structurally pure crystalline anhydrous lactitol by cooling a lactitol solution having a lactitol purity of no less than 80% (on DS content), preferably 90% or higher from a temperature at or slightly below 100° C. to a temperature at or slightly above 69° C. and by maintaining the supersaturation of said lactitol solution at a level of 1 to 8% (w/w) above the solubility line defined by the equation:

$s/\% = 59.6 + 0.3003t/°$ C.   Eq.(1)

wherein s is the solubility % (w/w) of anhydrous lactitol calculated from the mass of lactitol and water as follows: weight of lactitol/(weight of lactitol+weight of water)×100%;

t is the temperature in ° C.

The resulting anhydrous lactitol crystals are preferably recovered at a temperature above 66° C., and dried to provide pure crystalline anhydrous lactitol having a melting range of 146–152° C. and a moisture content of 0–0.5%.

The present invention also provides a process for crystallizing structurally pure crystalline lactitol monohydrate by cooling a lactitol solution having a lactitol purity of no less than 80% (on DS content), preferably 90% or higher from a temperature at or slightly below 69° C. to a temperature at or slightly above 53° C. and by maintaining the supersaturation of said lactitol solution at a level of 1 to 8% (w/w) above the solubility line defined by the equation;

$s/\% = 50.2 + 0.4346t/°$ C.   Eq.(2)

wherein s is the solubility % (w/w) of lactitol monohydrate calculated from the mass of lactitol and water as follows: weight of lactitol/(weight of lactitol+weight of water)×100%;

t is the temperature in ° C.

After the crystallization the crystals resulting in any respective stability area should preferably be recovered at a temperature close to the lowest temperature of said stability area. For instance, when producing lactitol monohydrate having a stability area of 69–53° C. the crystals are preferably removed above 50° C. This is done in order to make it easier to be sure that the recovered crystals are indeed monohydrate, without leaving to take extra precautions.

However, a person skilled in the art knows that in a crystallization procedure crystal growth will preferentially continue around crystals already present in the solution. Therefore, in a cooling crystallization such as the one described in EP 0 456 636 monohydrate crystals will continue to grow also below 53° C. due to the mass of pure monohydrate crystals in the solution. The crystallization at this stage should, however, not be prolonged and the cooling should be rapid.

The resulting lactitol monohydrate crystals are preferably dried to provide pure crystalline lactitol monohydrate having a melting range of 90–100° C. and a moisture content of 4.9–5.1%.

The present invention further provides a process for crystallizing structurally pure crystalline lactitol dihydrate by cooling a lactitol solution having a lactitol purity of no less than 80% (on DS content), preferably 90% or higher from a temperature at or slightly below 53° C. to a temperature at or slightly above 12° C. and by maintaining the supersaturation of said lactitol solution at a level of 1 to 8% (w/w) above the solubility line defined by the equation;

$$s/\% = 39.7 + 0.6332 t/° C. \quad \text{Eq. (3)}$$

wherein s is the solubility % (w/w) of lactitol dihydrate calculated from the mass of lactitol and water as follows: weight of lactitol/(weight of lactitol+weight of water)×100%;

t is the temperature in ° C.

The resulting lactitol dihydrate crystals are preferably recovered at a temperature above 12° C., and dried to provide pure crystalline lactitol dihydrate having a melting range of 72 to 75° C. and a moisture content of 9.4–9.6%.

The present invention further provides a process for crystallizing structurally pure crystalline lactitol trihydrate by cooling a lactitol solution having a lactitol purity of no less than 80% (on DS content), preferably 90% or higher from a temperature at or slightly below 12° C. to a temperature at or slightly above 0° C. and by maintaining the supersaturation of said lactitol solution at a level of 1 to 8% (w/w) above the solubility line defined by the equation;

$$s/\% = 33.4 + 1.1482 t/° C. \quad \text{Eq. (4)}$$

wherein s is the solubility % (w/w) of lactitol trihydrate calculated from the mass of lactitol and water as follows: weight of lactitol/(weight of lactitol+weight of water)×100%;

t is the temperature in ° C.

The resulting lactitol trihydrate crystals are preferably recovered at a temperature slightly above 0° C., and dried to provide pure crystalline lactitol trihydrate having a melting range of 38–45° C. and a moisture content of 13.4–13.8%.

The water content of the crystals is preferably measured by the Karl Fischer method. The melting range is preferably measured by a melting point microscope.

An accurate determination of the melting range of the lactitol crystals can be most successfully carried out by introducing samples of softly crushed crystals into several capillary tubes and melting the open ends of the tubes before measuring. The measurements are carried out with a conventional melting point apparatus at different constant temperatures using one capillary tube per measurement until the extreme points of the melting range are found.

When determining the melting point, one must take into account that, for instance, molten lactitol monohydrate has a high viscosity at its melting temperature, wherefore it takes time (even 2 minutes) before the sample is spread evenly on the walls of the capillary tube.

On account of its excellent technical and physiological properties, pure lactitol monohydrate is particularly suitable as a substitute for sugar diabetic, dietetic or tooth-friendly products. By combining lactitol monohydrate with other bulk or intense sweeteners, such as saccharin, Aspartame, Acesulfame K, Alitane, Sucralose, Stevioside or xylitol, a product highly resembling sugar and yet having a lower energy content and further being tooth-friendly can be prepared. This product can be used instead of sugar e.g. in sugar products, confectionery, jams, bakery products, table-top sweeteners, cereals, desserts, chocolate, beverage, chewing gum and ice-creams, as well as in pharmaceutical and cosmetical products, such as toothpaste.

Crystalline anhydrous lactitol is also suitable as a substitute for sugar in foodstuffs and sweets. The anhydrous lactitol may also be combined with other sweeteners such as saccharine and xylitol. The anhydrous lactitol is particularly suitable for the production of chocolate.

Lactitol dihydrate may also be used as a sweetener in foodstuffs, mostly in the same way as lactitol monohydrate and anhydrous lactitol. Due to its higher water content, lactitol dihydrate is slightly less hygroscopic than lactitol monohydrate. However, its lower melting point makes it useful in some applications, whereas lactitol monohydrate or anhydrous lactitol may be more suitable for some other uses.

The present invention provides a tool for knowing when any specific lactitol crystal form will be crystallized from a given lactitol solution at a specific temperature range. It gives the expert the stability areas which make it possible for the expert to produce pure crystals of the desired lactitol species. It provides a tool for the expert to monitor the temperature at any given concentration so as to maintain the supersaturation at a suitable level above the solubility graph of any of the lactitol hydrate or anhydrous forms.

The determination of the solubility and stability of lactitol crystals in water was made as follows:

Solubility Test 1

Materials and Methods

The lactitol, which was used in the tests, was high grade lactitol monohydrate Lactitol MC (batch 21769) manufactured by Xyrofin OY, Finland according to EP Patent 0456636. This monohydrate was also used as seed crystals. When lactitol dihydrate was studied at 45° C. and 55 ° C., lactitol dihydrate produced at the applicant's research laboratory Dec. 20, 1994 (crystallization No. 3) was used both for solution and as seed crystals. The water content of the lactitol dihydrate was 9.42% by weight by a colorimetric Karl Fischer method. The water, which was used, was distilled water.

For the determination of the solubility a solution with a supersaturation of 5 g/100 g of solution was made. At 35° C. the supersaturation was 10 g/100 g. Also at the temperatures of 5° C., 10° C. and 15° C. the supersaturation was 10 g/100 g, because supersaturation must be higher than the solubility of the monohydrate, which was used for seeding. The solutions were made by dissolving the monohydrate into water at a temperature above the solubility temperature. The solutions which were used at 65° C. and 75° C. were made by evaporating with a vacuum rotating flask evaporator. The concentrations were determined by refractometric indexes (RI). The weights of solutions are shown in Table 1. At the temperatures of 5° C., 10° C. and 15° C. the solutions were made in a 2-liter jacketed vessel. The other solutions were made in 200 ml or 250 ml measurement bottles.

When the lactitol had dissolved, the solution was cooled to the test temperature. The solution was seeded with softly crushed monohydrate crystals (2 tests with dihydrate crystals). The weights of the seed crystals are shown in Table 1. In the measurement bottles the solutions were stirred with a magnetic stirrer and in the jacketed vessel with a motor driven mixer.

TABLE 1

The weights of the solution components.

| Temperature, ° C. | lactitol mono-hydrate, g | water, g | seed, g | dry substance conc. of suspension, g/100 g |
|---|---|---|---|---|
| 5.1 | 493.33 | 419.40 | 13.14 | 52.0 |
| 10.2 | 530.02 | 360.04 | 10.06 | 57.0 |
| 15.0 | 805.70 | 540.00 | 12.78 | 57.2 |
| 25.6 | 140.85 | 80.18 | 2.38 | 60.9 |
| 35.0 | 152.14 | 50.02 | 2.13 | 71.7 |
| 44.8 | 195.61 | 60.01 | 2.69 | 72.9 |
| 55.0 | 229.40 | 50.00 | 2.96 | 78.2 |
| 65.0 | 315.38 | h | 2.64 | 81.4 |
| 74.8 | 238.82 | h | 2.75 | 86.6 |
| 45 | 203.64(dih) | 50.21 | 2.80(dih) | 72.8 |
| 55 | 425.79(dih) | 74.59 | 5.14(dih) | 78.8 | h = evaporated according to the RI
dih = dihydrate

The crystallization of lactitol and the equilibration of the solution was monitored by measuring the refractometric index (RI) of the mother liquid. Before taking a sample, the crystals were allowed settle on the bottom of the vessel, so that the measurement of the RI would be as exact as possible. The settling of crystals was slight due to the high viscosities of the lactitol solutions. Thus, the RI of the mother liquid was measured from a suspension of crystals and solution. At the end point of the measurement the waiting time was so long that the mother liquid was clearly separated and after that the RI of the mother liquid was measured. The RIs were measured below 55° C. with an Index Instruments GPR-11–37 refractometer and above 55° C. with a Zeiβ refractometer, both of which were calibrated.

The equilibration of the solution was generally monitored for 7 . . . 14 days, but only for 3 days, when dihydrate was used as seed crystals. At the end of the measurement the temperature of the solution was measured with a mercury thermometer, which had a measurement range 0 . . . 150° C. and reading accuracy of 0.2° C. The accuracy of this thermometer was checked against a calibrated thermometer.

After the crystal suspension had reached equilibrium, the crystals were separated by centrifuging 15 min 5000 rpm using a thick cloth. One part of the crystals was dried at 60° C. in a drying cabinet over a night. The water contents of both undried and dried crystals were analyzed by the Karl Fischer method or by a coulometric Karl Fischer method. Furthermore, melting behaviors were analyzed.

Results

The final solubilities at the studied temperatures are shown in Tables 2 and 3 in addition to the crystal forms. The crystal form was concluded from the water contents of the undried crystals and from the melting ranges. The water contents are shown in Tables 4 and 5 and melting behaviors in Table 6.

TABLE 2

The equilibrium solubilities of lactitol and the lactitol crystal forms, when lactitol monohydrate was used as seed crystals.

| Temp., ° C. | Solubility, g/100 g | Crystal form |
|---|---|---|
| 5.1 | 42.3 | trihydrate |
| 10.2 | 45.7 | dihydrate |
| 15.0 | 48.8 | dihydrate |
| 25.6 | 56.3 | dihydrate |
| 35.0 | 61.7 | dihydrate |
| 44.8 | 69.4 | mixture |
| 55.0 | 75.2 | monohydrate |
| 65.0 | 79.6 | monohydrate |
| 74.8 | 82.7 | anhydrous |

TABLE 3

The equilibrium solubilities of lactitol and the lactitol crystal forms, when lactitol dihydrate was used as seed crystals.

| Temp., ° C. | Solubility, g/100 g | Crystal form |
|---|---|---|
| 45.0 | 69.1 | dihydrate |
| 54.7 | 73.4 | monohydrate |

TABLE 4

The water contents of crystals as % by weight, when lactitol monohydrate was used as seed crystals.

| Temp. ° C. | Water content, % |
|---|---|
| 5.1 | 14.31 |
| 10.2 | 9.97 |
| 15.0 | 10.18 |
| 25.6 | 9.70 |
| 35.0 | 10.24 |
| 44.8 | 5.57 |
| 55.0 | 5.24 |
| 65.0 | 5.23 |
| 74.8 | 0.48 |

TABLE 5

The water contents of crystals as % by weight, when lactitol dihydrate was used as seed crystals.

| Temp., ° C. | Dried/60° C. |
|---|---|
| 45.0 | 8.9 |
| 54.7 | 5.14 |

TABLE 6

The melting point (m.p.) of the samples of the solubility test.

| Test temp., ° C. | m.p. ° C. |
|---|---|
| 5.1 | 59.1–60.5 |
| 10.2 | 75–80 |
| 15.0 | 72.2–72.5 |
| 25.6 | — |
| 35.0 | 74.6–75.8 |
| 44.8 | 94.5–95.8 |
| 55.0 | 97.5–100.6 |
| 65.0 | 95.3–97.2 |
| 74.8 | 152–153.1 |

The solubility data of Table 2 was combined with some earlier solubility measurement data. The curve fittings of the solubility points were made as linear fittings, when % by weight is used as a concentration unit. The solubilities of the hydrate forms in the crystallization areas were found to be almost linear. The fittings were made with the aid of the spread sheet program Excel 5.0$^R$. The solubility equations of the different hydrate forms are shown in Equations (I) to (IV):

$$\text{anhydrous:} \quad \frac{s}{g/100\ g} = 59.55 + 0.3003\ \frac{t}{°C.} \quad \text{Eq. (I)}$$

$$\text{monohydrate:} \quad \frac{s}{g/100\ g} = 50.21 + 0.4346\ \frac{t}{°C.} \quad \text{Eq. (II)}$$

$$\text{dihydrate:} \quad \frac{s}{g/100\ g} = 39.67 + 0.6332\ \frac{t}{°C.} \quad \text{Eq. (III)}$$

$$\text{trihydrate:} \quad \frac{s}{g/100\ g} = 33.41 + 1.1482\ \frac{t}{°C.} \quad \text{Eq. (IV)}$$

The fitting of the trihydrate cannot be considered absolutely exact because only three measurement points were used for fitting: one exact point, one uncertain point and one calculatory point.

Conclusions

The solubility points and the curve fittings are shown in a graph in FIG. 1. It is found that the curve fittings correspond to solubility points well. From the intersections of solubility curves it is possible to conclude the stability areas of the different lactitol forms. The stability areas of the different lactitol forms are found to be trihydrate: temperature<12° C. (not accurate)
dihydrate: 12° C.<temperature <53° C.
monohydrate: 53° C.<temperature <69° C.
anhydrous: temperature>69° C.

When seed crystals are used, the amount of seed crystals and the crystallization velocity have effect on the crystallization temperature areas, especially at lower boundaries of the stability areas.

The following instructive examples serve only to illustrate the working of the invention and should not be taken as limiting the same.

EXAMPLE 1

Cooling Crystallization; Lactitol Monohydrate

A crystallization is carried out for pure lactitol monohydrate, starting from a filtered and de-ionised lactitol solution. The lactitol solution is prepared from a lactose solution hydrogenated by the conventional technique.

The crystallization is carried out according to the following steps: A lactitol solution having a purity of about 98% lactitol in the dry matter is evaporated to 82% by weight at a temperature above 70° C., and transferred into a conventional horizontal cylindrical batch-operated cooling crystallizer provided with a mixer and a recycling water jacket whose temperature is controlled by means of a microprocessor. The crystallization is carried out by controlling the cooling rate so that the supersaturation of the mother liquor does not exceed 8%.

In the crystallizer, the temperature of the solution is adjusted to 69° C., whereafter the solution is seeded with crushed lactitol monohydrate crystals. The seed crystal size is 0.02–0–05 mm, and the quantity thereof is 0.004% by weight on the lactitol in the batch. After the seeding, the mass is cooled in 10 hours down to 53° C. at a constant cooling rate, while monitoring the supersaturation by measuring the refractometric index (RI). The supersaturation is maintained at not higher than 5–7% above the equation Eq. 2:

$$s/\% = 50.2 + 0.4346 t/°\ C.$$

The crystals are separated from the mother liquor at a temperature above 50° C. with a conventional basket centrifuge wherein the crystals are also washed using about 5% of water per obtained amount of crystal product. The centrifuged crystals are dried with a drum dryer using the conventional technique. The yield of lactitol monohydrate is about 40% by weight on lactitol in the batch.

The resulting lactitol monohydrate crystals have a melting point of 94–98° C. and a water content (Karl Fischer) of 5.0%.

Crystallization Example 1 is intended to illustrate the practicability of the process according to the invention, but the crystallization may also be carried out by modifying it in a manner as required by normal effective production operation. Thus, the crystallization may also be performed without adding seed crystals, i.e. by allowing the solution to form seeds spontaneously. Further, the crystallization may be effected in combination with an evaporative crystallization as demonstrated in Example 2. The crystallization may also be carried out in a continuous operation as long as the temperature is maintained in the range 69–53° C. and the supersaturation of the mother liquor is maintained below 8% (w/w).

EXAMPLE 2

Cooling Crystallization Combined with Evaporative Crystallization

Crystallization of lactitol monohydrate is performed starting from a lactitol solution prepared by hydrogenation as in Example 1. The solution is evaporatively crystallized for about 4 hours at 59 to 63° C., whereafter the crystallization mass is subjected to cooling crystallization from about 63° C. to 53° C. as described in Example 1.

For the evaporative crystallization the lactitol solution is concentrated in a conventional evaporation crystallizer at a pressure of about 180 mbar to a dry substance content of about 81% by weight. The solution is seeded with mildly crushed lactitol monohydrate crystals. After seeding, more feed solution is supplied to the crystallizer, and the evaporation is continued at 59 to 63° C. for about 4 hours. The resulting crystals are separated at 50.5° C. and dried as described in Example 1.

The crystallization is carried out by controlling the evaporation and cooling to keep a supersaturation of the mother liquor at less than 8%.

The lactitol monohydrate yield is about 60% by weight on lactitol of the batch. The lactitol monohydrate has a melting point of 94–98° C. and a water content of 5.0%

EXAMPLE 3

Cooling Crystallization; Anhydrous Lactitol

A lactitol solution containing about 98% of lactitol on dry solids is evaporated to a concentration of about 91% by weight at a temperature of about 95° C., and transferred into a conventional horizontal cylindrical batch-operated cooling crystallizer provided with a mixer and a recycling water jacket whose temperature is controlled by means of a microprocessor.

The cooling of the syrup is started at a rate of 10° C./15 hours under stirring and after some time crystals form. The cooling is continued until a temperature of 75° C. whereafter the crystals are centrifuged off, washed rapidly with water, and dried with a fluidization drier at about 65° C. Dried crystals are obtained at a yield of about 30%. The melting point of the crystals is 149° C. to 152° C., the water content is 0.2%.

The crystallization may also be effected in several steps, in which event a better yield is obtained.

During cooling the supersaturation is monitored by measuring the RI so as to ascertain that the supersaturation does not fall below the solubility equation (Eq. 1) for anhydrous lactitol. The supersaturation is maintained at no higher than about 6–8% (w/w) above said equation.

EXAMPLE 4

Cooling Crystallization; Lactitol Dihydrate

Lactitol dihydrate is crystallized from hydrogenated 98.5% purity lactitol syrup by cooling. Crushed lactitol dihydrate crystal seep are added at 50° C. and the cooling is continued to 15° C. The crystals are centrifuged to provide a yield of 52% and a crystal size of 0.9 mm. The crystals are dried at a temperature of about 50° C.

The lactitol dihydrate crystals formed have a melting point of 70–72° C. and a water content of 9.5%.

The supersaturation of the initial solution as well as the supersaturation during the cooling is monitored by measuring the RI so as to ascertain that the supersaturation does not fall below the solubility equation (Eq. 3) for lactitol dihydrate. The supersaturation is maintained at no higher than about 6–8% (w/w) above said equation.

EXAMPLE 5

Cooling Crystallization; Lactitol Trihydrate

Lactitol trihydrate is crystallized from a lactitol solution having a purity of about 98% by weight. Crushed lactitol trihydrate crystal seeds are added at 10° C. and the cooling is continued to 0° C. The crystals are centrifuged to provide a yield of 30%. The crystals are dried over $MgSO_4$ and are found to melt at 40–43° C. The water content is 13.6%.

The concentration of the initial lactitol solution as well as that of the solution during the cooling is monitored by measuring the RI so as to ascertain that the supersaturation does not fall below the solubility equation (Eq. 4) for lactitol trihydrate. The supersaturation is maintained at no higher than about 6–8% (w/w) above said equation.

In order to increase the yield, the above described cooling crystallization is repeated in several steps while monitoring the supersaturation.

What is claimed is:

1. A process for the crystallization of lactitol from an aqueous lactitol solution having a lactitol purity of no less than 80% (on DS content), comprising crystallizing structurally pure crystalline lactitol forms selected from the group consisting of anhydrous, monohydrate, dihydrate and trihydrate by cooling said lactitol solution from a temperature at or slightly below the highest temperature of the stability area of the respective crystalline lactitol form to a temperature at or slightly above the lowest temperature of the stability area of said crystalline lactitol form, said stability areas being defined, respectively, within the temperature limits of 100° C. and 0° C. by the intersections of the solubility lines defined by the following equations (1) to (4):

anhydrous: $s/\%=59.6+0.3003t/°$ C.   Eq.(1)

monohydrate $s/\%=50.2+0.4346t/°$ C.   Eq.(2)

dihydrate: $s/\%=39.7+0.6332t/°$ C.   Eq.(3)

trihydrate: $s/\%=33.4+1.1482t/°$ C.   Eq.(4)

wherein s is the solubility % (w/w) of each respective lactitol form calculated from the mass of lactitol and water as follows: weight of lactitol/(weight of lactitol+weight of water)×100%;

t is the temperature in ° C.;

and by maintaining the supersaturation of said lactitol solution at a level of 1 to 8% (w/w) above the solubility line of the respective lactitol form crystallizing in said area.

2. A process according to claim 1 wherein said supersaturation is maintained at the desired level by monitoring the lactitol percentage of said lactitol solution and adjusting the temperature accordingly.

3. A process according to claim 2 wherein said lactitol content is monitored by measuring the refractometric index of said lactitol solution.

4. A process according to claim 1 wherein said lactitol solution is seeded at the start of the crystallization with small crystals of the crystalline lactitol form which is to be crystallized in the respective stability area.

5. A process according to claim 1 wherein said cooling crystallization is preceded by an evaporation crystallization at a temperature well within the stability area of the crystallizing lactitol form, while maintaining the supersaturation at 1 to 8% (w/w) or less.

6. A process according to claim 1 wherein the crystals resulting from the crystallization in any respective stability area are recovered at a temperature close to the lowest temperature of said stability area and dried.

7. A process according to any one of the preceding claims 1 to 6 comprising crystallizing structurally pure crystalline anhydrous lactitol by cooling said lactitol solution from a temperature at or slightly below 100° C. to a temperature at or slightly above 69° C. and by maintaining the supersaturation of said lactitol solution at a level of 1 to 8% (w/w) above the solubility line defined by the equation:

$s/\%=59.6+0.3003t/°$ C.   Eq. (1)

wherein s is the solubility % (w/w) of anhydrous lactitol calculated from the mass of lactitol and water as follows: weight of lactitol/(weight of lactitol+weight of water)×100%;

t is the temperature in ° C.

8. A process according to claim 7 comprising recovering the resulting anhydrous lactitol crystals at a temperature above 66° C., and drying them to provide pure crystalline anhydrous lactitol having a moisture content of 0–0.5% (w/w).

9. A process according to any one of the preceding claims 1 to 6 comprising crystallizing structurally pure crystalline lactitol monohydrate by cooling said lactitol solution from a temperature at or slightly below 69° C. to a temperature at or slightly above 53° C. and by maintaining the supersaturation of said lactitol solution at a level of 1 to 8% (w/w) above the solubility line defined by the equation;

$s/\%=50.2+0.4346t/°$ C.   Eq.(1)

wherein s is the solubility % (w/w) of lactitol monohydrate calculated from the mass of lactitol and water as follows: weight of lactitol/(weight of lactitol+weight of water)×100%;

t is the temperature in ° C.

10. A process according to claim 9 comprising recovering the resulting lactitol monohydrate crystals at a temperature above 50° C., and drying them to provide pure crystalline lactitol monohydrate having a moisture content of 4.9–5.1% (w/w).

11. A process according to any one of the preceding claims 1 to 6 comprising crystallizing structurally pure crystalline lactitol dihydrate by cooling said lactitol solution from a temperature at or slightly below 53° C. to a temperature at or slightly above 12° C. and by maintaining the supersaturation of said lactitol solution at a level of 1 to 8% (w/w) above the solubility line defined by the equation;

$$s/\% = 39.7 + 0.6332t/° C. \quad \text{Eq.(3)}$$

wherein s is the solubility % (w/w) of lactitol dihydrate calculated from the mass of lactitol and water as follows: weight of lactitol/(weight of lactitol+weight of water)×100%;

t is the temperature in ° C.

12. A process according to claim 11 comprising recovering the resulting lactitol dihydrate crystals at a temperature above 12° C., and drying them to provide pure crystalline lactitol dihydrate having a moisture content of 9.4–9.6% (w/w).

13. A process according to any one of the preceding claims 1 to 6 comprising crystallizing structurally pure crystalline lactitol trihydrate by cooling said lactitol solution from a temperature at or slightly below 12° C. to a temperature at or slightly above 0° C. and by maintain the supersaturation of said lacritol solution at a level of 1 to 8% (w/w) above the solubility line defined by the equation;

$$s/\% = 33.4 + 1.1482t/° C. \quad \text{Eq. (4)}$$

wherein s is the solubility % (w/w) of lactitol trihydrate calculated from the mass of lactitol and water as follows: weight of lactitol/(weight of lactitol+weight of water)×100%;

t is the temperature in ° C.

14. A process according to claim 13 comprising recovering the resulting lactitol trihydrate crystals at a temperature of about 0° C., and drying them to provide pure crystalline lactitol trihydrate having a moisture content of 13.4–13.8% (w/w).

15. The process according to claim 1, wherein said crystallization of lactitol from an aqueous lactitol solution has a lactitol purity of 90% or higher.

* * * * *